(12) United States Patent
Linden

(10) Patent No.: US 6,303,619 B1
(45) Date of Patent: Oct. 16, 2001

(54) META-SUBSTITUTED ACIDIC 8-PHENYLXANTHINE ANTAGONISTS OF A3 HUMAN ADENOSINE RECEPTORS

(75) Inventor: Joel M. Linden, Charlottesville, VA (US)

(73) Assignees: University of Virginia; University of Virginia Patent Foundation, both of Charlottesville ( * ) Notice: Subject to any disclaimer, the term of this patent is extended or adjusted under 35 U.S.C. 154(b) by 0 days.

(21) Appl. No.: 09/038,991

(22) Filed: Mar. 12, 1998

(51) Int. Cl.$^7$ ................................................. A61K 31/52
(52) U.S. Cl. ............................................................ 514/263
(58) Field of Search ............................................. 514/263

(56) References Cited

FOREIGN PATENT DOCUMENTS

| 0203721 | * | 12/1986 | (EP) . |
| 2264948A | * | 9/1993 | (GB) . |
| 90/00056 | * | 1/1990 | (WO) . |
| 95/11681 | * | 5/1995 | (WO) . |

OTHER PUBLICATIONS

Biaggioni, I., et al., "Adenosine Produces Pulmonary Vasoconstriction in Sheep: Evidence for Thromboxane A2/Prostaglandin Endoperoxide–receptor Activation", *Circ. Res.,* (1989).*
Bjorck, T., et al., "Isolated Bronchi from Asthmatics are Hyper Responsive to Adenosine", *Am. Rev. Respir. Dis.,* vol. 145, 1087–1091, (1992).*
Bradford, M.M., "A Rapid and Sensitive Method for the Quantitative of Microgram Quantities of Protein Utilizing the Principle of Protein–Dye Binding", *Anal. Biochem.,* 72, 248–254, (1976).*
Bruns, R.F., et al., *Proc. Natl. Acad. Sci. USA,* vol. 80, 2077–2080, (1983).*
Cheng, Y.C., et al., *Biochem. Pharmacol.,* vol. 22, 3099–3108, (1973).*
Graham, F.L., et al., "A New Technique for the Assay of Infectivity of Human Adenovirus 5 DNA", *Virology,* vol. 52, 456–467, (1973).*
Hannon, J.P., et al., "A Role for Mast Cells in Adenosine A3 Receptor–Mediated Hypotension in the Rat", *Br. J. Pharmacol.,* vol. 115, 945–952, (1995).*
Heller, L.J., et al., "Effect of Adenosine on Histamine Release and Atrioventricular Conduction During Guinea Pig Cardia Anaphylaxis", *Circ. Res.,* vol. 62, 1147–1158, (1988).*
Ito, B.R., et al., "Role of Cardiac Mast Cells In Complement C5a–induced Myocaridal Ischemia", *Am. J. Physiol.,* vol. 264 (Heart Circ. Physiol. 33), H1346–H1354, (1992/1993).*
Jacobson, K.A., et al., *J. Med. Chem.,* vol. 32, 1043–1051, (1989).*
Jarvis, M.F., et al., *J. Pharmcaol. Exp. Ther.,* vol. 251, 888–893, (1989).*

Jin, X., et al., "Inosine Binds to A3 Adenosine Receptors and Stimulates Mast Cell Degranulation", *J. Clin. Invest.,* vol. 100, 2849–2857, (1997).*
Jolly, S.R., et al., "Effects of Lodoxarnide on Ischemic Reperfused Myocardium", *J. Cardiovas. Pharmacol.,* vol. 4, 441–448, (1982).*
Keller, A.M., et al., "Acute Reoxygeneration Injury in the Isolated Rat Heart: Role of Resident Cardiac Mast Cells", *Circ. Res.,* vol. 63, 1044–1052 (1988).*
Libert, F., et al., *Biochem. Biophys. Res. Comm.,* vol. 187, 919–926, (1992).*
Lichtenstein, L., *Sci. Am.,* vol. 269, 116–125, (1993).*
Linden, J., et al., "Molecular Cloning and Functional Expression of a Sheep A3 Adenosine Receptor with Widespread Tissue Distribution", *Mol. Pharmacol,* vol. 44, 524–532, (1993).*
Lohse, et al., *N.S. Arch. Pharmacol.,* vol. 335, 555–560, (1987).*
Luneau, et al., *FEBS Letters,* vol. 1, 163–167, (1991).*
Marquardt, et al., *J. Immunol.,* vol. 120, 871–878, (1978).*
McPherson, G.A., *Computer Programs for Biomedicine,* vol. 17, 107–114, (1983).*
Meyerhof, W., et al., "Molecular Cloning of a Novel Putative G–protein Coupled Receptor Expressed During Rat Spermiogenesis", *Febs Lett,* vol. 284, 155–160, (1991).*
Ramkumar, V., et al., "The A3 Adenosine Receptor is the Unique Adenosine Receptor which Facilitates Release of Allergic Mediators in Mast Cells", *J. Biol. Chem.,* vol. 268, 16887–16890, (1993).*
Raud, J., *Acta. Physiol. Scand.,* vol. 135 (Suppl. 578), 1–58, (1989).*
Rivkees, S.A., "Localization and Characterization of Adenosine Receptor Expression in Rat Testis", *Endocrinology,* vol. 135, 2307–2313, (1994).*
Robeva, A.S., et al., "Molecular Characterization of Recombinant Human Adenosine receptors", *Drug Dev. Res.,* vol. 39, 243–252, (1996).*
Rosenblum, W.I., *Brain Re.,* vol. 49, 75–82, (1973).*
Salvatore, C.A., et al., "Molecular Cloning and Characterization of the Human A3 Adenosine Receptor", *Proc. Natl. Acad. Sci. USA,* vol. 90, 10365–10369, (1993).*
Sambrook, J., et al., "Molecular Cloning, a Laboratory Manual, 2nd Edition", *Cold Spring Harbor Press,* Cold Spring Harbor, NY, pp. 16.3–16.31, 16.56–16.58, 17.2–17.25, 17.36–17.37, (1989).*
Sanger, F.S., et al., *Proc. Natl. Acad. Sci. USA,* vol. 74, 5463–5467, (1977).*
Schild, H.O., *Pharm. Rev.,* vol. 9, 242–246, (1957).*

(List continued on next page.)

Primary Examiner—Rebecca Cook
(74) Attorney, Agent, or Firm—Schwegman, Lundberg, Woessner & Kluth, P.A.

(57) ABSTRACT

The invention concerns the use of a xanthine or a xanthine derivative having a meta-substituted acidic aryl at the 8-position to specifically modulate the physiologic role of adenosine activation of its various receptors.

8 Claims, 3 Drawing Sheets

OTHER PUBLICATIONS

Ukena, D., et al., "Species Differences in Structure–Activity Relationships of Adenosine Agonists and Xanthine Antagonists at Brain A1 Adenosine Receptors", *Febs. Lett.,* vol. 209(1), 122–128, (1986).*

Van Caulker, D., et al., *J. Neurochem.,* vol. 33, 999–1003, (1979).*

Wan, W., et al., *J. Neurochem.,* vol. 55, 1763–1771, (1990).*

Wolff, A.A., et al., "Ventricular Arrhythmias Parallel Cardiac Histamine Efflux After Coronary Artery Occlusion in the Dog", *Agents and Actions,* vol. 25, 296–306, (1988).*

Zhou, Q.Y., et al., "Molecular Cloning and Characterization of an Adenosine Receptor: the A3 Adenosine Receptor", *Proc. Natl. Acad. Sci. USA,* vol. 89, 7432–7436, (1992).*

Van Caulker, D., Muller, M. and Hamprecht, B. (1979) *J. Neurochem.* 33, 999–1005.*

Bruns, R.F., Lu, G.H. and Pugsley, T.A. (1986) *Mol. Pharmacol.* 29, 331–346.*

Wan, W., Sutherland, G.R. and Geiger, J.D. (1990) *J. Neurochem.* 55, 1763–1771.*

Linden, J., Jacobson, M.A., Hutchins, C. and Williams, M. (1994) Adenosine Receptors in Handbook of Receptors and Channels, vol. 1. G Protein–Linked Receptors, ed Peroutka, D.J. (CRC Press, Boca Raton. Fl.), pp. 29–43.*

Meyerhof, W., Muller–Brechlin, R. and Richter, D. (1991) *FEBS Lett.* 284, 155–160.*

Zhou, Q–Y, Chuanyi, L., Olah, M.E., Johnson, R.A., Stiles, G.L. and Civelli, (1992) *Proc. Natl. Acad. Sci. USA* 89 7432–7436.*

Linden, J. Taylor, H.E., Robeva, A.S., Tucker, A.L. Stehle, J.H., Rivkees, S.A., Fink, S.J. and Reppert, S.M., (1993) *Mol. Pharm.* 44:524–532.*

Libert, F., Van Sande, J., Lefort, A., Czemilofsky, A., Dumont, J.E., Vassart, G., Ensinger, H.A. and Mendla, K.D. (1992) *Biochem. Biophys .Res. Comm.* 187, 919–926.*

Furlong, T.J., Pierce, K.D., Selbie, L.A. and Shine, J. (1992) *Mol Brain. Res.* 15, 62–66.*

Pierce, K.D., Furlong, T.J., Selbie, L.A. and Shine, J. (1992) *Biochem. Biophys. Res. Comm.* 187, 86–93.*

Linden, J., Patel, A. and Sadek, S. (1985) *Cir. Res.* 56, 279–284.*

Linden, J., Patel, A., Earl, C.Q., Craig, R.H. and Daluge, S.M. (1988) *J. Med. Chem.* 31, 745–751.*

Feinberg, A. and Vogelstein., B. (1983) *Anal. Biochem.* 132, 6–13.*

Mumby, S.M., Heukeroth, R.O., Gordon, J.I. and Gilman, A.G. (1990) *Proc. Natl. Acad. Sci. USA* 87, 728–732.*

Mahan, L.C., McVittie, L.D., Smyk–Randall, E.M., Nakata, H., Monsma, F.J., Gerfen, C.R. and Silbey, D.R. (1991) *Mol. Pharmacol.* 40, 1–7.*

Hamilton, B.R. and Smith, D.O. (1991) *J. Physiol.* (Lond.) 432, 327–341.*

Schild, H.O. (1957) *Pharm. Rev.* 9, 242–246.*

Strosberg, A.D. (1991) *Eur. J. Biochem.* 196, 1–10.*

O'Dowd, B.F., Hnatowich, M., Caron, M.G., Lefkowitz, R.J. and Bouvier, M. (1989) *J. Biol Chem.* 264, 7564–7569.*

Dodd, P.R., Watson, W.E.J., and Johnston, G.A.R. (1986) *Clin. Exp. Pharmacol. Physiol.* 13, 711–722.*

Schiffmann, S.N., Libert, F., Vassart, G. and Vanderhaeghen, J.J. (1991) *Neurosci. Lett.* 130, 177–181.*

Peet, N.P., Lentz, N.L., Meng, E.C., Dudley, M.W., Ogden, A.M.L.,Demeter, D.A., Weintraub, H.J.R. and Bey, P. (1990) *J. Med Chem.* 33, 3127–3130.*

Van der Wenden, E.M., IJzerinan, A.P. and Soudijn, W. (1992) *J. Med Chem.* 35, 629–635.*

Stehle, J.H., Rivkees, S.A., Lee, JJ., Weaver, D.R., Deeds, J.D. and Reppert, S.M. (1992) *Mol. Endocrinol.* 6, 384–393.*

Fozzard, J.R. and Carruthers, A.M. (1993) *Br. J. Pharmacol.* 109, 3–5.*

Neely, C.F., Kadowitz, P.J., Lippton, H., Neiman, M. and Hyman, A. (1989) *J. Pharmacol. Exp. Ther* 250, 170–176.*

Konduri, G.G., Woodward, L.L., Mukhopadhyay, A. and Deslunukh, D.R. (1992) *Am. Rev. Respir. Dis.* 146, 670–676.*

Cushley, M.J., Tattersfield, A.E. and Holgate, S.T. (1984) *Am. Rev. Respir. Dis.* 129, 380–384.*

* cited by examiner

META-SUBSTITUTED ACIDIC 8-PHENYLXANTHINE ANTAGONISTS OF A3 HUMAN ADENOSINE RECEPTORS

BACKGROUND OF THE INVENTION

1. Field of the Invention

The present invention relates to methods for the treatment or prevention of disease states induced by activation of the A3 receptor and mast cell activation.

2. Discussion of the Related Art

Adenosine is a naturally occurring nucleoside which exhibits diverse and potent physiological actions in the cardiovascular nervous, pulmonary, renal and immune systems. Adenosine produces bronchoconstriction in asthmatics but not in nonasthmatics by triggering mast cell degranulation (Cushly et al., 1984, *Am. Rev. Respir. Dis.* 129:380–384). This suggests that the activation of an adenosine receptor contributes to bronchoconstriction in asthmatics.

The amino acid sequence for the human A3 receptor is 72% identical with the rat A3 receptor and 85% identical with the sheep A3 receptor sequences.

The actions of adenosine are mediated through G-protein coupled receptors, the A1, A2A, A2B and A3 adenosine receptors. The degranulation of rat mast cells has been attributed to the activation of A3 receptors (Ramkumar V, Stiles G L, Beaven M A and Ali H (1993), "The A3 Adenosine Receptor Is the Unique Adenosine Receptor Which Facilitates Release of Allergic Mediators in Mast Cells," *J Biol Chem* 268(23):16887–216890). The adenosine receptors were initially classified into A1 and A2 subtypes on the basis of pharmacological criteria and coupling to adenylate cyclase (Van Caulker, D., Muller, M. and Hamprecht, B. (1979) *J. Neurochem.* 33, 999–1003.). Further pharmacological classification of adenosine receptors prompted subdivision of the A2 class into A2A and A2B subtypes on the basis of high and low affinity, respectively, for adenosine and the agonists NECA and CGS-21680 (Bruns, R. F., Lu, G. H. and Pugsley, T. A. (1986) *Mol. Pharmacol.* 29, 331–346; Wan, W., Sutherland, G. R. and Geiger, J. D. (1990) *J. Neurochem.* 55, 17631771). The existence of A1, A2A and A2B subtypes has been confirmed by cloning and functional characterization of expressed bovine, canine, rat and human receptors.

A fourth subtype, A3, had remained pharmacologically undetected until its recent identification by molecular cloning. The rat A3 sequence, tgpcrl, was first cloned from rat testis by Meyerhoff et al. (Meyerhof W, Müller-Brechlin R and Richter D (1991) Molecular Cloning of a novel putative G-protein coupled receptor expressed during rat spermiogenesis. *Febs Lett* 284:155–160.). Subsequently, a cDNA encoding the identical rat receptor was cloned from striatum and functionally expressed by Zhou et al. (Zhou Q Y, Li C, Olah M E, Stiles G L and Civelli O (1992), "Molecular cloning and characterization of an adenosine receptor: the A3 adenosine receptor," *Proc Natl Acad Sci USA* 89:7432–7436.). When compared to the other members of the G-protein coupled receptor family, the rat sequence had the highest homology with the adenosine receptors (>40% overall identity, 58% within the transmembrane regions). When stably expressed in CHO cells, the receptor was found to bind the radioligand $^{125}$I-APNEA (N$^6$-2-(4-amino-3-iodophenyl)ethyladenosine) and when transfected cells were treated with adenosine agonists, cyclic AMP accumulation was inhibited with a potency order of NECA=R-PIA>CGS21680. The rat A3 receptor exhibited a unique pharmacology relative to the A1 and A2 adenosine receptor subtypes and was reported not to bind the xanthine antagonists 1,3-dipropyl-8-phenylxanthine (DPCPX) and xanthine amine congener (XAC). Messenger RNA for the rat A3 adenosine receptor is also primarily expressed in the testis.

The sheep homolog of the A3 receptor was cloned from hypophysial pars tuberalis (Linden J, Taylor H E, Robeva A S, Tucker A L, Stehle J H, Rivkees S A, Fink J S and Reppert S M (1993). "Molecular cloning and functional expression of a sheep A3 adenosine receptor with widespread tissue distribution," *Mol Pharmacol* 44:524–532.). The sheep receptor is 72% identical to the rat receptor, binds the radioligand $^{125}$I-ABA and is coupled to inhibition of cyclic AMP. The agonist affinity order of the sheep receptor is I-ABA>APNEA>NECA≧R-PIA>>CPA. The pharmacology of xanthine antagonists was extensively studied and, contrary to what had been found in the rat, the sheep receptor was found to exhibit high affinity for 8-phenylxanthines with para-acidic substitutions. Also, in contrast to the rat where transcript is primarily located in testis, the transcript for the sheep A3 adenosine receptor is widespread throughout the brain and is most abundant in the lung and spleen. In sheep moderate amounts of transcript are also observed in pineal and testis. Thus, because the published literature provides an inconsistent profile of adenosine A3 receptor pharmacology and tissue distribution, it was not possible to predict the pharmacology or tissue distribution of the human A3 adenosine receptor.

Based on the use of tissue rich in particular adenosine receptor subtypes, assays have been described to identify adenosine receptor agonists and antagonists and determine their binding affinity (see GB 2 264 948 A, published Sep. 15, 1993; see also R. F. Brans et (al., (1983) *Proc. Natl. Acad. Sci. USA* 80:2077–2080; R. F. Bruns et al., (1986) *Mol. Pharmacol.* 29:331–346; M. F. Jarvis et al. (1989) *J. Pharma. Exp. Therap.* 251:888–893; K. A. Jacobson et (al., (1989) *J. Med. Chem.* 32:1043–1051). The properties of human receptors can be studied using recombinant human receptors (Robeva A S, Woodard R, Jin X, Gao Z, Bhattacharya S, Taylor H E, Rosin D L and Linden J (1996), "Molecular characterization of recombinant human adenosine receptors," *Drug Dev Res* 39: 243–252.; Salvatore C A, Jacobson M A, Taylor H E, Linden J and Johnson R G (1993), "Molecular cloning and characterization of the human A3 adenosine receptor," *Proc Natl Acad Sci USA* 90:10365–10369.)

8-Phenylxanthines, methods of their synthesis and their use in human and veterinary therapy for conditions associated with the cell surface effects of adenosine have been described (EP 0 203 721, published Dec. 3, 1986). However, this publication is silent as to adenosine receptor subtypes and subtype specificity of disclosed compounds. In WO 90/00056, a group of 1,3-unsymmetrical straight chain alkyl-substituted 8-phenylxanthines were described as being potent bronchodilators. This disclosure is likewise silent as to the receptor subtype specificity of disclosed compounds.

Methods of treating conditions related to the physiological action of adenosine have, to date, proven inferior due to the presence of multiple subtypes present in the animal tissue utilized (R. F. Bruns et al., (1986) *Mol. Pharm.* 29:331–346) and the differences between species in the affinity for adenosine analogs and the physiological effects of adenosine (Ukera et al., (1986) *FEBS Lett,* 209:122–128).

SUMMARY OF THE INVENTION

The present invention concerns the use of compounds identified as specific modulators of adenosine's physiological actions. The pharmacology of these compounds is characterized through the use of cloned human adenosine receptors of the A1, A2A, A2B and A3 class and their subtypes. Compounds identified as antagonists of the A3 adenosine receptor subtype are useful in preventing mast cell degranulation and are therefore useful in the treatment or prevention of disease states induced by activation of the A3 receptor and mast cell activation. These disease states include but are not limited to asthma, myocardial reperfusion injury, allergic reactions including but not limited to rhinitis, poison ivy induced responses, urticaria, scleroderm arthritis, other autoimmune diseases and inflammatory bowel diseases.

Although the human A1, A2A and A2B adenosine receptor cDNAs have been cloned, the tissue distribution of human adenosine receptor transcripts has not been previously presented. Through Applicant's ongoing research, the characterization of a human A3 adenosine receptor subtype, and the pharmacological profile of the human A3 adenosine receptor and the human tissue distribution of the A3 transcript has been described.

Through the use of homogenous, recombinant adenosine receptors, the identification and evaluation of compounds which have selectivity for a single receptor subtype have now been accomplished. Moreover, because of the variable effects of adenosine documented in other species, the utilization of human adenosine receptor subtypes is advantageous for the development of human therapeutic adenosine receptor agonists, antagonists or enhancers. Applicant has found that there exist compounds which unexpectedly exhibit selective binding affinity for the human A3 adenosine receptor, and a method of using such compounds has been developed to overcome the disadvantages of using compounds of uncharacterized specificity. The compounds specifically block activities mediated through the activation of the A3 receptor subtype without substantially blocking the activities of other adenosine receptor subtypes.

DETAILED DESCRIPTION OF THE INVENTION

Figure 1:
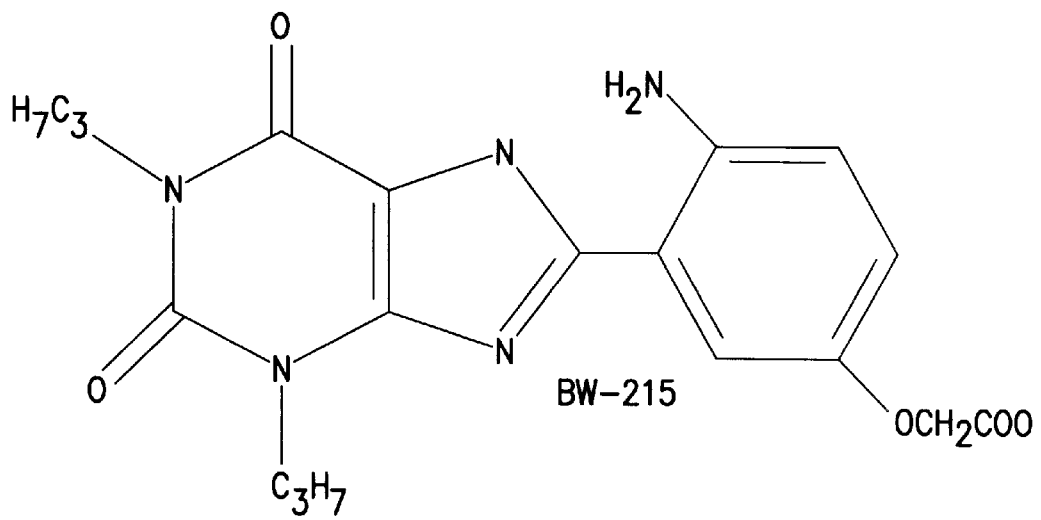
FIG. 1 shows the structures of meta-substituted 8-phenylxanthine derivatives.
Figure 1:
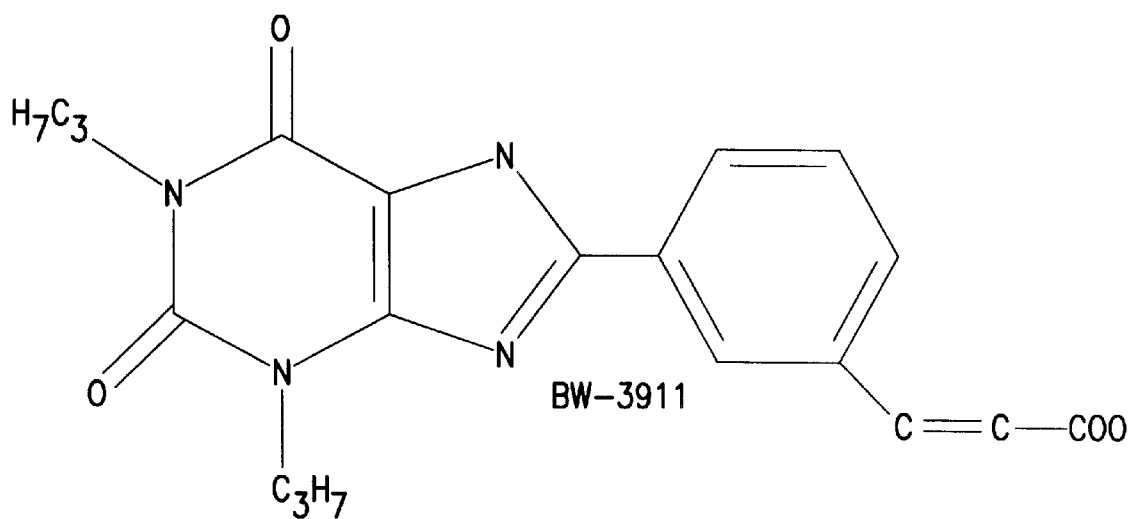

Applicant has identified compounds through the use of recombinant human adenosine receptors A1, A2A, A2B and A3, and functional assays, that specifically modulate the physiologic effects of adenosine activation of its various receptors. The human A3 adenosine receptor from a striatal cDNA library can be cloned using a probe derived from the homologous rat sequence. The cDNA encodes for a protein of 318 amino acids and exhibits 72% and 85% overall identity with the rat and sheep A3 adenosine receptor sequences, respectively. Specific and saturable binding of the adenosine receptor agonist, $^{125}$I-N$^6$-aminobenzyladenosine ($^{125}$-ABA) was measured on the human A3 receptor stably expressed in CHO cells with a KD=10 nM. The potency order for adenosine receptor agonists was determined to be N-ethylcarboxamidoadenosine (NECA)≧R-phenylisopropyladenosine (R-PIA)>N$^6$-cyclopentyladenosine (CPA)>S-p-benylisopropyladenosine (S-PIA). The human receptor was found to be blocked by xanthine antagonists. A partial listing of the pharmacology is that the potency order of antagonists is I-ABOPX>1,3-dipropyl-8-(4-acrylate) phenylxanthine (BW-A1433)≧xanthine amino cogener (XAC)>>1,3-dipropyl-8-cyclopentylxanthine (DPCPX). Adenosine, NECA, R- and S-PIA and CPA inhibited forskolin-stimulated cAMP accumulation by 30–40% in the stably transfected CHO cells; I-ABA is a partial agonist. When measured in the presence of antagonists, the dose response curves of NECA-induced inhibition of forskolin-stimulated cAMP accumulation were right-shifted. Antagonist potencies determined by Schild analyses correlated well with those established by competition for radioligand binding. The tissue distribution of transcripts for all of the human adenosine receptor subtypes was compared. The A3 adenosine receptor transcript is widespread, and in contrast to the A1, A2A and A2B transcripts, the most abundant expression is found in the lung and liver. By comparison, the rat A3 adenosine receptor transcript is primarily expressed in testis and the sheep transcript is most abundant in the lung, spleen and pineal. The human tissue distribution of A3 mRNA is more similar to the widespread profile found in sheep than to the restricted profile found in the rat. Numerous physiological effects of adenosine may be mediated by A3 adenosine receptors in man.

Applicant has found that, in a method for achieving specific blockade of the A3 subtype of the adenosine receptor, adenosine, adenosine analogs, inosine (Jin X, Shepherd R K, Duling B R and Linden J (1997), "Inosine binds to A3 adenosine receptors and stimulates mast cell degranulation," *J Clin Invest* 100:2849–2857.) and other A3 adenosine receptor agonists induce mast cell degranulation in an animal model and that this can be prevented by selective antagonists of the A3 receptor. The release of enzymes, bioactive amines and arachidonic acid metabolites following mast cell activation causes vasoconstriction, edema, leukocyte accumulation, and ultimately, tissue damage. Mast cell degranulation is a component of myocardian reperfusion injury, hypersensitivity reactions (asthma, allergic rhinitis, and urticaria), ischemic bowel disease, autoimmune inflammation, and atopic dermatitis. Selective A3 adenosine receptor antagonists can be used to treat or prevent these diseases and pathologic effects that result from mast cell degranulation.

Applicant has further found that other physiologic effects induced through activation of the A3 adenosine receptor are amenable to modulation through blockade of A3 adenosine mediated responses in basophils, eosinophiles and other immune cells. Mast cell degranulation is clearly involved in the pathophysiology of allergies Such as asthma. Autoimmune diseases are also characterized by immune reactions which attack targets, including self-proteins in the body such as collagen, mistaking them for invading antigens. The resulting damage, caused at least in part by mast cell degranulation, is amenable to treatment by the method of this invention which comprises administration of selective A3 adenosine receptor antagonists effective to inhibit mast cell degranulation. Among these types of diseases, all of the following, but not limited to these, are amenable to treatment by the above-discussed method: Addison's disease (adrenal), autoimmune hemolytic anemia (red cells), Crohn's disease (gut), Goodpasture's syndrome (kidney and lungs), Grave's disease (thyroid), Hashimoto's thyroiditis (thyroid), idiopathic thrombocytopinic purpura (platelets), Insulin-dependent diabetes militus (pancreatic beta cells), multiple sclerosis (brain and spinal cord), myasthenia gravis (nerve/muscle synapses), *Pemphigus vulgaris* (skin), pernicious anemia (gastric parietal cells), poststreptococcal glomerulonephritis (kidney), psoriasis (skin), rheumatoid arthritis (connective tissue), sclerodenna (heart, lung, gut, kidney), Sjogren's syndrome (liver, kidney, brain, thyroid, salivary gland), spontaneous, infertility (sperm), and systemic lupus erythematosus (DNA, platelets, other tissues).

The above-discussed method provides a means for preventing or treating disease states associated with vascular constriction induced through activation of the A3 subtype of the adenosine receptor. The method comprises contacting the receptor in the vasculature with an amount of a compound which selectively blockades activation of the A3 adenosine receptor subtype. In one embodiment, this blockade occurs on granulocytes, including mast cells and other tissues in lung that express A3 receptors. The method extends to the treatment or prevention of disease states mediated through activation of the A3 subtype of the adenosine receptor on mast cells. Disease states associated with A3 adenosine receptor activation and mast cell degranulation include, but are not limited to asthma, myocardial reperfusion injury, allergic reactions including but not limited to rhinitis, asthma, poison ivy induced responses, urticaria, scleroderma, arthritis, and inflammatory bowel diseases.

In a preferred embodiment of the method, an A3 adenosine receptor antagonist will have a pKi for the A3 subtype of 7 or greater, and a pKi for other adenosine receptor subtype of 6 or less. Xanthine compounds having the following characteristics are preferred: An acidic, aromatic substitution at the 8-position of the xanthine (the acidity decreases affinity to A1 subtype to below a pKi of about 6, and the aromatic substitution reduces the affinity for the A2 subtype to below about 6). By further modifying the xanthine to include an aromatic, and preferably a halogenated aromatic at the xanthine 3 position, these trends in binding affinity are accentuated.

From these studies, the use of a class of xanthines and their derivatives having the following characteristics is defined as having selective binding properties for the primate (including human) A3 adenosine receptor:

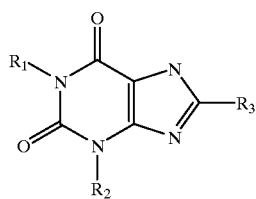

wherein $R_1$ is a substituted or unsubstituted alkyl, alkenyl or cycloalkyl, $R_2$ is aryl, substituted aryl, hetero-aryl or substituted hetero-aryl, and $R_3$ is an acidic aryl or substituted acidic aryl. In specific embodiments of the method, the xanthine is selected from the group consisting of IABOPX, BW-A1433 and BW-A3911.

I-ABOPX: $R_1$=propyl; $R_2$=4-amino-3-iodo-benzyl; $R_3$=phenyl-4-oxyacetic acid BW-A1433: $R_1$=propyl; $R_2$=propyl; $R_3$=phenyl-4-acrylate BW-A3911: $R_1$=propyl; $R_2$=propyl; $R_3$=phenyl-3-acrylate The present invention is directed to the discovery of a series of compounds that are the most potent and selective xanthine antagonists of human A3 adenosine receptors yet discovered. The compounds are xanthines or xanthine derivatives having a meta-substituted acidic aryl at the 8-position and a substituted or unsubstituted aryl, alkyl or alkenyl substituent at the 3 position. Switching from para to meta substitution of the 8-phenyl substituent increases selectivity of the 8-phenylxanthines for A3 adenosine receptors by decreasing affinity for the other adenosine receptor subtypes A1, A2A and A2B.

In the ongoing research of the Applicant, a comparison was conducted of the distribution among tissues of human adenosine receptor transcripts and suggests that the A1, A2A, A2B and A3 subtypes are all expressed in a number of tissues, but the pattern of transcript distribution is variable. Within the four tissues analyzed, A1 and A2A adenosine receptor transcripts are highly expressed in the brain. In contrast, the human A3 adenosine receptor transcript is most abundant in the lung and liver.

Prior to the above-described method, the physiological role of the A3 adenosine receptor was not defined. Recently, a receptor exhibiting an agonist pharmacological profile thought to be characteristic of the rat A3 subtype and insensitive to blockade by 8-(para-sulfophenyl)theophylline, was suggested to mediate in vivo hypotension in the angiotenisin II-supported circulation of the pithed rat (Hannon J P, Pfannkuche H J and Fozard J R (1995), "A role for mast cells in adenosine A3 receptor-mediated hypotension in the rat," *Br J Pharmacol* 15:945–952.). The effect of 8-(para-sulfophenyl)theophylline on the cloned rat A3 receptor has not been evaluated and further pharmacological characterization is required to determine if the rat receptor binds this antagonist. 8-Para-(sulfophenyl)theophylline has broad action on A1, A2A and A2B adenosine receptor subtypes (Ukena D, Jacobson K A, Padgett W L, Ayala C, Shamim M T, Kirk K L, Olsson R A and Daly J W (1986), "Species differences in structure-activity relationships of adenosine agonists and xanthine antagonists at brain A1 adenosine receptors," *Febs Lett* 209(1):122–128.), and also blocks both the human and sheep A3 receptors. Another possible physiological role for the A3 adenosine receptor subtype in reproduction and spermatogenesis has been proposed on the basis of the abundant transcript found in rat testis and the in situ localization of mRNA within the central luminal regions of seminiferous tubules where sperm maturation occurs (Rivkees S A (1994), "Localization and characterization of adenosine receptor expression in rat testis," *Endocrinology* 135:2307–2313.). It is possible that A3 adenosine receptors also are involved in the maturation of sperm in human and ovine testis, since low to moderate levels of receptor transcript are found in these species, respectively.

The abundant mRNA observed in the human and sheep lung is evidence that the A3 adenosine receptor subtype mediates a physiological action in the pulmonary system. Adenosine has been shown to mediate both vasodilation and vasoconstriction (Biaggioni I, King L S, Enayat N, Robertson D and Newman J H (1989), "Adenosine produces pulmonary vasoconstriction in sheep: Evidence for thromboxane A2/prostaglandin endoperoxide-receptor activation," *Circ Res.*) in the pulmonary vasculature. In asthmatics, but not in normal patients, adenosine produces bronchoconstriction which can be antagonized by theophylline (Cushley M J, Tattersfield A E and Holgate S T (1984), "Adenosine-induced bronchoconstriction in asthma. Antagonism by inhaled theophylline," *Am Rev Respir Dis* 129:380–384.). The establishment of the pharmacological profile for the A3 receptor in both the human and the sheep, and the availability of subtype selective ligands facilitates the identification of the physiological functions mediated by the A3 adenosine receptor subtype and the treatment of disease states mediated through agonism of this receptor subtype.

Adenosine has been shown to produce bronchoconstriction in asthmatics but not in nonasthmatics, demonstrating that adenosine plays a role in the etiology of this disease state (Cushly et al., 1984, *AM. Rev. Respir. Dis.* 129:380–384). Adenosine mediated bronchoconstriction in asthmatics is blocked by a combination of histamine and leukotriene antagonists (Bjorck et al., *Am. Rev. Resp. Dis.* 1992, 145:1087–1091). This indicates that adenosine acts by releasing histamine, leukotriene and other agents from mast cells or other cells that contain these allergic mediators. Thus compounds identified by Applicant's research that selectively antagonize the A3 adenosine receptor are concluded to be used in conjunction with other therapies. This includes co-administration of anti-histamine, leukotriene blockade or other anti-allergic mediator therapies and A3 specific antagonists. The presence of the rat A3 adenosine receptor on rat RBL-2H3 mast cells, activation of which results in potentiation of the histamine secretary response to antigen (Ramkumar et al., *J. Biol. Chem.* 268:16887–16890, 1993) is evidence in the rat of the role of these receptors in that animal. However, because of the reportedly different pharmacology of the rat A3 receptor contrasted to that of the human and sheep A3 receptors, it could not be predicted that the A3 receptor was significant in primates including humans.

It has been reported that adenosine potentiates the release of granule contents from mast cells isolated from rat peritoneum (Lohse et al., *N.S. Arch. Pharmacol.* 335:555–560, 1987; Marquardt et al., *J. Immunol.* 120:871–878, 1978), and that mast cell degranulation causes constriction in some vascular beds resulting in C5a-induced myocardial ischemia (Ito et al., *Am. J. Physiol.* 264 (*Heart Circ. Physiol.* 33):HI 346-H 1354, 1993), mast cell dependent inflammation (Raud, J., *Acta. Physiol. Scand.* 135 (Suppl. 578):I-58, 1989), brain arteriole diameter constriction (Rosenblum, W. I., *Brain Res.* 49:75–82, 1973), and the release of allergic mediators (Ramkumar et al., *J. Biol. Chem.* 268:16887–16890, 1993). Accordingly, in demonstrating inhibition of mast cell degranulation, applicant has invented a treatment or preventative method that is demonstrated for all of the above known and many yet to be defined disease states associated with adenosine induced mast cell degranulation.

The trigger for mast cell degranulation is usually thought to be an allergen. Allergens are endocytosed by marcrophages and degraded. The resulting fragments are displayed on T lymphocytes. B lymphocytes are stimulated to mature into plasma cells which are able to secrete allergen-specific molecules known as immunoglobulin E (IgE). These antibodies attach to receptors on mast cells in tissue and on basophils circulating in blood to trigger degranulation (see L. Lichtenstein, *Sci. Am.* 269:116–125, 1993). As will be described below, the activation of A3 adenosine receptors can produce mast cell degranulation and enhance the effect of allergens. Adenosine and antigens trigger an influx of calcium to induce mast cell granules to release their contents and promote synthesis and release of cytokines, prostaglandins and leukotrienes. The various chemicals released by mast cells are responsible for many allergic symptoms. Long term release of these chemicals can induce basophils, eosinophils, and other cells flowing through blood vessels to migrate into the tissue. Migration is promoted due to the expression and activation of adhesion molecules on the circulating cells and on vascular endothelial cells. The circulating cells adhere to the endothelial cells, roll among them, and eventually cross into the surrounding matrix. These recruited cells secrete chemicals of their own that damage tissue. Thus, there are long term secondary effects which may also be prevented by specific blockade of mast cell degranulation.

Applicant has found that the specific blockade of the A3 subtype of the adenosine receptor is effective to block the vasoconstrictive response induced through adenosine activation of this receptor subtype. Further, the use of a specific inhibitor of the A3 adenosine receptor subtype is effective to inhibit effects induced by adenosine mediated mast cell degranulation, and has therefore shown that disease states including but not limited to myocardial ischemia (Ito et al., *Am. J. Physiol.* 264 (*Heart Circ. Physiol.* 33):H1346–H1354, 1993), mast cell dependent inflammation (Rand, J., *Acta. Physiol. Scand.* 135 (Suppl. 578): 1–58, 1989), brain arteriole diameter constriction (Rosenblum, W. I., *Brain Res.* 49:75–82, 1973), and the release of allergic mediators (Ramkumar et al., *J. Biol. Chem.* 268:16887–16890, 1993), are all amenable to prevention and treatment by contacting A3 receptor bearing mast cells with an amount of a selective A3 inhibitor effective to prevent mast cell degranulation.

Another embodiment of the above-described method is directed to prevention or treatment of myocardial ischemia/ reperfusion. The basis of this application of the method is that a period of myocardial ischemia followed by reperfusion produces damage to the myocardium. Part of this damage may be secondary to mast cell degranulation triggered by adenosine during ischemia. This suggests that A3 adenosine receptor antagonists may be useful for the treatment of patients prone to reperfusion injury. This includes patients with coronary artery diseases in general, and patients about to have occluded arteries opened (reperfused) by various interventions (coronary artery bypass grafts, angioplasty or thrombolytic therapy). Adenosine-induced mast cell degranulation during a period of transient ischemia may be responsible for the phenomenon of preconditioning (i.e. a transient ischemic episode reduces myocardial damage resulting from a subsequent prolonged ischemic episode). Accordingly, mast cells are temporarily depleted of damaging mediators during the preconditioning period. These observations are supported by reports suggesting that mast cell degranulation is involved in ischemia/reperfusion injury. See for example Heller, L. J. and Regal, J. F., "Effect of adenosine on histamine release and atrioventricular conduction during guinea pig cardia anaphylaxis," *Circ. Res.* 62:1147–1158, 1988. Hence, increases in levels of endogenous adenosine during cardiac anaphylaxis contributes to the development of atrioventricular conduction delays and increases in levels of adenosine before antigen challenge may increase the amount of histamine released during cardiac anaphylactic reactions; Wolff, A. A. and Levi, R., Ventricular arrhythmias parallel cardiac histamine efflux after coronary artery occlusion in the dog, *Agents and Actions* 25:296–306, 1988. Further, during acute myocardial ischemia, the coronary sinus histamine concentration increases simultaneously with the development of early ischemic ventricular arrhythmias and in proportion to their severity; Keller, A. M. Clancy, R. M., Baff, M. L. Marboe, C. C. and Cannon, P. J., "Acute reoxygenation injury in the isolated rat heart: role of resident cardiac mast cells," *Circ. Res.* 63:1044–1052, 1988. Further, the isolated crystalloid-perfused rat heart is not a leukocyte-free preparation and mast cells resident to the heart play an important role in acute reoxygeneration injury; Jolly, S. R., Abrams, G. D., Romson, J. L., Bailie, M. B. and Lucchesi, B. R., "Effects of Iodoxarnide on ischemic reperfused myocardium," *J. Cardiovas. Pharmacol.* 4:441–448, 1982. Further, lodoxamide, a drug that acts to inhibit mast cells degranulation, reduces myocardial ischemic injury; Ito, B. R., Engler, R. L., Del Balzo, U., "Role of cardiac mast cells in complement C5a-induced myocardial ischemia." *Am. J. Physiol.* 33:H1346–H1354, 1992. Hence, cardiac mast cells are involved in complement-induced release of vasoactive eicosanoids, including TxA2.

Again during ongoing research by the Applicant, the human A1, A2A, A2B and A3 receptor subtype cDNAs were subcloned into the expression vectors pSVL (PHARMACIA), CMV5 (Mumby et al. 1990, *PNAS,* 87:728–732) or pREP (INVITROGEN). Transient expression in COS7 cells (monkey kidney cell line, ATCC CRL 1651, ATCC, Rockville, Md.) was accomplished by transfection of the cloned adenosine receptor cDNAs under the control of the SV40 promoter into mammalian cells (e.g., COS7). Membranes prepared from the transfected cells were utilized for the determination of binding affinity, selectivity and specificity of the human adenosine receptors for various ligands. Stable expression of the human adenosine receptors in mammalian cells (e.g., CH0, HEK 293) was achieved after integration of the transfected cDNA into the chromosomes of the host cells. These stable cell lines constituently express the cloned human adenosine receptors and can be propagated infinitely. Stable cell lines expressing the human adenosine subtype cDNAs individually can be used in the binding assay to measure the affinity and selectivity of the receptors for adenosine agonists, antagonists and enhancers.

Membranes prepared from transfected COS7 cells were utilized in a binding assay to measure the affinity of the human adenosine receptors for the radiolabeled adenosine agonists, [3H]-cyclohexyladenosine (CHA), [3H]-CGS21680 (2-(p-(2-carboxyethyl)phenylamino)-5'-N-ethylcarboxamidoadenosine), [3H]-5'-N-ethylcarboxamido adenosine ([3H]-NECA), or [$^{125I}$]-N$^6$-aminobenzyl adenosine ($^{125}$I-ABA). Monolayer cell culture of transfected COS7 cells were dissociated with 1 mM EDTA in phosphate buffered saline and resuspended in 5 mM Tris, pH7.6/10 mM MgCl2. The cells were subjected to freeze-thaw lysis and the suspension was homogenized in a glass dounce homogenizer. The membranes were pelleted, resuspended in binding buffer, 50 mM Tris pH 7.6/10 mM MgCl2 and incubated with adenosine deaminase before the binding assay. The binding assay was performed by incubating 50–100 Fg of membranes with increasing concentrations of radiolabeled adenosine agonists. Bound ligand was separated from free ligand by filtration on a SKATRON CELL HARVESTER equipped with a receptor binding filtermat. Bound radioactivity was measured by scintillation counting. Substances which bind to or enhance binding to expressed human adenosine receptors in COS and CHO cells can be identified in competition binding assays with radiolabeled adenosine or xanthine analogs. For the competition binding assay, membranes were incubated with 5 nM [3H]-CHA, 5 nM [3H]-CGS21680 or 10 nM [3H]-NECA and various concentrations of adenosine agonists or antagonists.

A transient expression system in Xenopus oocytes was established by microinjection of in vitro transcribed mRNA from the cloned adenosine receptor cDNAs. The expression system allows the measurement of the biological effects (i.e., changes in cAMP levels) upon activation of the expressed adenosine receptors with ligand binding. The cAMP levels are measured by a radioimmunoassay (RIANEN kit, DuPont/NEN) using the acetylation protocol. Activations of the expressed receptors by ligand binding are coupled to either increases or decreases in the intracellular cAMP levels dependent upon the subtype of adenosine receptor (Van Calker et at., (1979) *J. Neurochem.* 33:999–1003; Londos et rat. (1980) *Proc. Natl. Acad. Sci. USA* 77:2551–2554). The activity of any potential adenosine receptor agonist can be evaluated by measuring the changes in cAMP levels in oocytes infected with adenosine receptor mRNA but not in uninfected or negative control injected oocytes. The activity of any potential adenosine receptor antagonist can be evaluated by determining the inhibition of the cAMP response induced by adenosine in oocytes injected with adenosine receptor transcripts but not negative control or uninfected oocytes. The changes in cAMP accumulation can alternatively be measured in stably transfected CHO cells expressing the human adenosine receptor subtypes.

The cAMP accumulation assay has a number of advantages over the binding assay established in the mammalian cell expression system as a screen for adenosine receptor modulating agents. The assay allows the measurement of a biological effect (i.e., changes in cAMP levels) resulting from activation of the expressed receptors by ligand binding. The native agonist adenosine is utilized in the assay to activate the expressed receptors. The functionality of additional adenosine receptor subtypes identified by molecular cloning, which may not have defined ligands for binding analysis, can be evaluated with the natural agonist and without prior identification of a selective, high affinity, radiolabeled ligand.

According to the method of this invention, an adenosine A3 specific antagonist which may comprise a xanthine or a xanthine derivative having a meta-substituted acidic aryl at the 8- position and a substituted or unsubstituted aryl, alkyl or alkenyl substituent at the 3 position is administered in an amount effective to induce blockade of the receptor. The higher the affinity of the antagonist for the receptor, the lower the required dosage. Compounds having a pKi of greater than about 7 for the A3 receptor and below about 6 for other adenosine receptor subtypes, may be administered by any effective means to achieve either localized or systemic contact of the antagonist with target A3 adenosine receptors. This might include intravenous, intramuscular, intrasynovial, intranasal, nebulized intrapulmonary, intraperitoneal or other common means for administration of therapeutic compounds. Dosages of between about 1 µg/kg and 10 mg/kg are envisioned, as necessary, to achieve the desired effect of A3 adenosine receptor blockade.

The meta substituted compounds of the present invention are surprisingly improved in selectivity for the A3 receptor site. While applicant does not intend to be bound by this mechanism, it is believed that switching from para to meta substitution increases the selectivity of the 8-phenylxanthines for the A3 adenosine receptors primarily by decreasing the affinity of the metal compounds for the other adenosine receptor subtypes, A1, A2A and A2B.

Included in the present invention are methods (1) for achieving blockade of the mast cell degranulation response induced through adenosine activation of the A3 adenosine receptor subtype, (2) for treating or preventing myocardial ischemia, inflammation, brain arteriole diameter constriction, and the release of allergic mediators, (3) for preventing or treating asthma, bronchoconstriction, allergic potentiation, inflammation or reperfusion injury in a human and (4) for preventing pro-inflammatory effects of adenosine mediated by A3 receptors. The methods comprise administering an amount of the adenosine A3 receptor specific inhibitor comprising a xanthine or a xanthine derivative having a meta-substituted acidic aryl at the 8- position to antagonize activation of the adenosine receptor of the A3 subtype by adenosine.

The methods include (5) achieving blockade of microvascular constriction and systemic hypotension induced through activation of the A3 subtype of the adenosine receptor, (6) treating an autoimmune disease selected from the group consisting of Addison's disease (adrenal), autoimmune hemolytic anemia (red cells), Crohn's disease (gut), Goodpasture's syndrome (kidney and lungs), Grave's disease (thyroid), Hashimoto's thyroiditis (thyroid), idiopathic thrombocytopinic purpura (platelets), Insulin-dependent diabetes militus (pancreatic beta cells), multiple sclerosis (brain and spinal cord), myasthenia gravis (nerve/muscle synapses), *Pemphigus vulgaris* (skin), pernicious anemia (gastric parietal cells), poststreptococcal glomerulonephritis (kidney), psoriasis (skin), rheumatoid arthritis (connective tissue), scleroderma (heart, lung, gut, kidney), Sjogren's syndrome (liver, kidney, brain, thyroid, salivary gland), spontaneous infertility (sperm), and systemic lupus erythematosus (DNA, platelets, other tissues), and (7) treating or preventing disease states mediated through activation of the A3 subtype of the adenosine receptor on mast cells by prevention of mast cell degranulation through blockade of the A3 subtype of the adenosine receptor. The treated disease state associated with method (7) includes asthma, myocardial reperfusion injury, allergic reactions including but not limited to rhinitis, poison ivy induced responses, urticaria, scleroderma, arthritis, and inflammatory bowel diseases.

The meta-substituted 8-phenylxanthine has the formula:

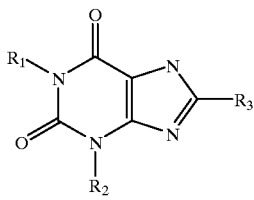

wherein $R_1$ is a substituted or unsubstituted alkyl, alkenyl or cycloalkyl, $R_2$ is aryl, substituted aryl, hetero-aryl or substituted hetero-aryl, and $R_3$ is an acidic aryl or substituted acidic aryl. The aryl can be benzyl or phenyl, the substituted aryl can be an aryl substituted with an alkyl, amino or halogen, the substituted hetero-aryl can be a hetero-aryl substituted with an alkyl, amino or halogen and the substituted acidic aryl can be an acidic aryl substituted with a carboxylate, oxyacetate, acrylate, sulphonate, phosphonate or tetrazol. In a preferred embodiment, $R_1$ is lower alkyl, $R_2$ is benzyl, halogenated benzyl, amino-benzyl or halogenated amino-benzyl, and $R_3$ is benzyl-acid. In a more preferred embodiment, $R_1$ is —$C_3H_7$, —$CH_3$ or —$C_2H_5$, $R_2$ is —$C_3H_7$, benzyl, halogenated benzyl, aminobenzyl or halogenated aminobenzyl and $R_3$ is —$CH_2$—$C_6H_4$—O-acid, $CH_2$—COO— or indole.

The preferred meta-substituted 8-phenylxanthines of the methods of the invention have an affinity for the A3 subtype of the human adenosine receptor which is at least one order of magnitude greater than the affinity for either the A1, A2A or A2B subtypes of the human adenosine receptor effective to antagonize activation of the adenosine receptor of the A3 subtype by adenosine. Further, the preferred meta-substituted 8-phenylxanthine has a pKi for the A3 subtype of 7 or greater and a pKi for other adenosine receptor subtypes of 6 or less. Most preferred meta-substituted 8-phenylxanthines include BW-215 and BW-3911. The structures of some preferred meta-substituted 8-phenylxanthines are shown in FIG. 1.

Adenosine is a potent vasodilator that has also been shown to cause vasoconstriction. The constrictor response has classically been attributed to A1 adenosine receptor stimulation or interactions with the renin-angiotensin system. Applicant's research has identified a previously unreported vasoconstrictor action of adenosine in hamster cheek pouch anerioles, along with the specific blockade of this response by A3 adenosine receptor antagonists. In the present invention, specific blockade of the A3 subtype of the adenosine receptor by a meta-substituted phenylxanthine is effective to block the vasoconstrictive response induced through adenosine activation of this receptor subtype. The use of a meta-substituted phenylxanthine specific inhibitor of the A3 adenosine receptor subtype is effective to inhibit effects induced by adenosine mediated mast cell degranulation, and that disease states including but not limited to myocardial ischemia (Ito et al., *Am. J. Physiol.* 264 (Heart Circ. Physiol. 33):H I 346-H 1354, 1993), mastcell-dependent inflammation (Raud, J., *Acta. Physiol. Scand.* 135 (Suppl '578):I-58, 1989), brain arteriole diameter constriction (Rosenblum, W. I., *Brain Res.* 49:75–82, 1973), and the release of allergic mediators (Ramkumar et al., *J. Biol. Chem.* 268:16887–16890, 1993), are all amenable to prevention and treatment by contacting A3 receptor bearing mast cells with an amount of a meta-substituted phenylxanthine selective A3 inhibitor effective to prevent mast cell degranulation.

The following examples are provided to further define but not to limit the invention defined by the foregoing description and the claims which follow:

EXAMPLE 1

Binding Studies

Membranes were prepared from transiently transfected COS7 cells 48 h after transfection or from G418-selected stably transfected CHO or HEK 293 cells. Cells were harvested in 1 mM EDTA in phosphate buffered saline and centrifuged at 2000×g for 10 minutes. The cell pellet was washed once with phosphate buffered saline. The cell pellet was resuspended in 2 mL of 5 mM Tris, pH 7.6/5 mM MgCl2. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM MgCl2, in a glass dounce homogenizer with 20 strokes. The membranes were pelleted at 40,000×g at 4° C. for 20 minutes. The membrane pellet was resuspended at a protein concentration of 1–2 mg/mL in binding assay buffer, 50 mM Tris, pH 7.6/10 mM MgCl2. Protein concentration was determined by tie method of Bradford ((1976) Anal. Biochem. 72: 248–250). Before the binding assay was performed, the membranes were incubated with adenosine deaminase (BOEHRINGER MANNHEIM), 2 U/mL for 30 minutes at 37EC. Saturation binding of [3H]-cyclohexyladenosine (CHA) was performed on membranes prepared from pSVLA1 transfected COS7 or CHO cells.

Membranes (100 µg) were incubated in the presence of 0.2 U/mL adenosine deaminase with increasing concentrations of CHA (NEN, 32 Ci/mmol) in the range of 0.62–30 nM for 120 minutes at 25° C. in a total volume of 500 µl. The binding assay was terminated by rapid filtration and three washes with ice-cold 50 mM Tris,pH 7.6/10 mM $MgCl_2$ on a SKATRON CELL HARVESTER equipped with a receptor binding filtermat (SKATRON INSTRUMENTS, INC). Non-specific binding was determined in the presence of 100 uM $N^{6}$-cyclopentyladenosine (CPA). Bound radioactivity was measured by scintillation counting in READY SAFE SCINTILLATION COCKTAIL (BECKMAN). For competition binding experiments, membranes were incubated with 5 nM [3H]-CHA and various concentrations of A1 adenosine receptor agonists. Saturation binding of [3H] CGS-21680 was performed on membranes prepared from pSVLA2A transfected COS7 cells. Membranes (100 µg) were incubated in the presence of 0.2 U/mL adenosine deaminase with increasing concentrations of CGS21680 (NEN, 48.6 Ci/mmol) in the range of 0.62–80 nM for 90 minutes at 25° C. in a total volume of 500 µl. The binding assay was terminated by rapid filtration with three washes with ice-cold 50 mM Tris, pH 7.6/10 mM $MgCl_2$ on a Skatron cell harvester equipped with a receptor binding filtermat (SKATRON INSTRUMENTS, INC). Non-specific binding was determined in the presence of 100 FM CPA. Bound radioactivity was measured by scintillation counting in READY SAFE LIQUID SCINTILLATION COCKTAIL (BECKMAN). For competition binding experiments, membranes were incubated with 5 nM [3H]-CGS21680 and various concentrations of A2 adenosine receptor agonists.

Saturation binding of [3H]5'-N-ethylcarboxamidoadenosine (NECA) was performed on membranes (100 µg) prepared from pSVLhb32C (A2B) transfected COS7 cells in the presence of adenosine deaminase with increasing concentrations of NECA (NEN, 15.1 Ci/mmol) in the range of 1.3–106 nM for 90 minutes at 25° C. in a total volume of 500 µl. The assay was terminated by rapid filtration and three washes with ice-cold binding buffer on a cell harvester equipped with a receptor binding filtermat (SKATRON INSTRUMENTS, INC). Bound radioactivity was measured by scintillation counting. Non-specific binding was measured on membranes prepared from non-transfected COS7 cells. For competition binding experiments, membranes from transfected cells were incubated with 10 nM [3H]NECA and varying concentrations of adenosine receptor antagonists.

EXAMPLE 2

The human A3 adenosine receptor was cloned from a human striata cDNA library. Oligonucleotide probes were designed based on the rat A3 sequence of Zhou et al., *Proc. Natl. Acad. Sci.* 89, 7432 (1992). The complete sequence of the human A3 adenosine receptor was determined and the protein sequence deduced. The cloned human A3 adenosine receptor is expressed in a heterologous expression system in COS, CHO and HEK 293 cells. Radiolabeled adenosine receptor agonists and antagonists are used to measure the binding properties of the expressed receptor. Stable cell lines can be used to evaluate and identify adenosine receptor agonists, antagonists and enhancers.

STEP A

A synthetic probe homologous to the rat A3 adenosine receptor was generated using the polymerase chain reaction (PCR). Three ul of rat brain cDNA was used as template in a PCR amplification reaction according to the GENEAMP protocol (PERKIN ELMER CETUS, Norwalk, Conn.) containing 50 pmol of primers 207 (5'-cccaagcttatgaaagccaacaatacc) and 208 (5'-tgctctagactctggtatcttcacatt) in a total volume of 50 ul. Primers 207 and 208 are based on the published rat A3 adenosine receptor sequence (Zhou et al, (1992), *Proc. Natl. Acad. Sci. USA,* 89:7432–7406). Forty cycles of 40 sec at 94° C., 1 min at 55° C., 3 min at 72° C. were performed and the resulting 788 bp fragment was subcloned into HindIII-XbaI digested pBLUESCRIPT II KS+ (STRATAGENE, La Jolla, Calif.). The sequence was verified by the SEQUENASE protocol (USBC, Cleveland, Ohio).

STEP B

The 788 bp PCR fragment was labeled with α32P-dCTP using the MULTIPRIME DNA LABELLING SYSTEM (AMERSHAM, Arlington Heights, Ill.) and used to screen a human striata cDNA library (STRATAGENE, La Jolla, Calif.). *E. coli* strain XL-1 Blue (STRATAGENE, La Jolla, Calif.). Cells were infected with library phage and grown overnight at 37° C. Phage DNA was transferred to HYBOND-N nylon filters according to the manufacturer's protocol (AMERSHAM, Arlington Heights, Ill.). The probe was incubated with the filters in 5×SSC, 30°% formamide, 5×Denhardt's solution, 0.5% sodium dodecyl sulfate, and 50 µg/ml sonicated salmon testis DNA. The filters were washed in 2×SSC at 55° C. A positively hybridizing phage (HS-21a) was identified and plaque purified by two additional rounds of plating and hybridization. The insert was subcloned to the plasmid pBLUESCRIPT II SK—according to the manufacturer's protocol (STRATAGENE, La Jolla, Calif.). Upon sequence analysis using the SEQUENASE protocol (USBC, Cleveland, Ohio) it was determined that clone HS-21a contained the complete open reading frame corresponding to the human homolog of the rat A3 adenosine receptor. The coding region of the human A3 adenosine receptor cDNA is 78% identical to the rat sequence at the nucleotide level and contains 265 bp and 517 bp of 5' and 3' untranslated sequence, respectively. The 1.7 kb fragment was excised using sites present in the multiple cloning site of pBLUESCRIPT II SK—(STRATAGENE, La Jolla, Calif.) and subcloned into Xhol/SacI digested pSVL (PHARMACIA, Piscataway, N.J.) for its expression in COS and CHO cells.

EXAMPLE 3

Mammalian Cell Expression

COS7 cells (ATCC #1651-CRL) were grown in complete medium, Dulbecco's modified Eagles's medium, DMEM (GIBCO, Grand Island, N.Y.) containing 10% fetal bovine serum, 100 U/mL penicillin-streptomycin and 2 mM glutainine, in 5% $CO_2$ at 37° C. Transient transfection of COS7 cells was performed by the $CaPO_4$ method (Graham, F. L. and Van Der Erb, A. J. (1973) Virology 52:456–567) using the Mammalian Transfection Kit (STRATAGENE). Plasmid DNA (15 µg) was precipitated with 125 mM $CaCl_2$ in BBS (N,N-bis(2-hydroxyethyl)-2-aminoethanesulfonic acid buffered saline) at room temperature for 30 minutes. The DNA precipitate was added to the COS7 cells and incubated for 18 h in 5% $CO_2$ at 37° C. The precipitate was removed and the cells were washed twice with serum free DMEM. Cells were incubated in complete medium in 5% $CO_2$ at 37° C. for 48 h prior to the binding assay.

Stable expression in CHO cells:

To establish stable cell lines, CHO cells were cotransfected with 20 µg of PSVL containing the adenosine receptor cDNA and 1 µg of pWLneo (STRATAGENE) containing the neomycin gene. Transfection was performed by the $CaPO_4$ method. DNA was precipitated at room temperature for 30 minutes, added to the COS7 cells and incubated 18 h in 5% $CO_2$ at 37° C. The precipitate was removed and the cells were washed twice with serum free DMEM. Cells were incubated for 24 h in 5% $CO_2$ at 37° C., replated in 24-well dishes at a dilution of 1:10, and incubated an additional 24 h before adding selection medium, DMEM containing 10% fetal bovine serum, 100 U/mL penicillin-streptomycin, 2 mM glutamine and 1.0 mg/mL G418 (GIBCO). Transfected cells were incubated at 5% $CO_2$, 37° C. until viable colonies were visible, approximately 14–21 days. Colonies were selected and propagated. The cell clone with the highest number of human adenosine receptors was selected for subsequent application in the binding assay.

EXAMPLE 4

Binding Assay

Membranes were prepared from transiently transfected COS7 cells 48 11 after transfection or from G418-selected stably transfected CHO or HEK 293 cells. Cells were harvested in 1 mM EDTA in phosphate buffered saline and centrifuged at 2000×g for 10 minutes. The cell pellet was washed once with phosphate buffered saline. The cell pellet was resuspended in 2 mL of 5 mM Tris, pH 7.6/5mM $MgCl_2$. Membranes were prepared from the cells by freeze-thaw lysis in which the suspension was frozen in a dry ice/ethanol bath and thawed at 25° C. twice. The suspension was homogenized after adding an additional 2 mL of 5 mM Tris, pH 7.6/5 mM $MgCl_2$, in a glass dounce homogenizer with 20 strokes. The membranes were pelleted at 40,000×g at 4° C. for 20 minutes. The membrane pellet was resuspended at a protein concentration of 1–2 mg/mL in binding assay buffer, 50 mM Tris, pH 7.6/10 mM $MgCl_2$. Protein concentration was determined by the method of Bradford ((1976) *Anal. Biochem.* 72: 248–250). Before the binding assay was performed, the membranes were incubated with adenosine deaminase (BOEHRINGER MANNHEIM), 2 U/mL for 30 minutes at 37° C. Saturation binding of $[^{125}I]$-$N^6$-aminiobenizyladenosine (125I-ABA) or $[^{125}I]$-$N^6$-2-(4-amino-3-iodophenyl)ethyladenosine (APNEA) was performed on membranes prepared from pSVLA3 transfected COS7 cells. Membranes (100 μg) were incubated in the presence of 0.2 U/mL adenosine deaminase with increasing concentrations of $^{125}I$-ABA in the range of 0.1–30 nM for 120 minutes at 25° C. in a total volume of 500 μl. The binding assay was terminated by rapid filtration and three washes with ice-cold 50 mM Tris, pH 7.6/10 mM $MgCl_2$ on a Skatron cell harvester equipped with a receptor binding flitermat (SKATRON INSTRUMENTS, INC). Non-specific binding was determined on non-transfected cells. Bound radioactivity was measured by scintillation counting in Ready Safe Scintillation Cocktail (BECKMAN).

EXAMPLE 5

In Vitro Transcription and Oocyte Expression

A 1.3 kb XhoI-BamHI fragment of the pSVL expression construct containing the full length human A2A adenosine receptor coding sequence was ligated into SalI-SpeI digested pGEMA (Swanson, et al, (1990) *Neuron* 4:929–939). The resulting plasmid, pGEMA2, was linearized with NotI, forming a template for in vitro transcription with T7 RNA polymerase. The homologous adenosine receptor subtype cDNA in pBluescript SK— was used as a template for in vitro transcription by T3 polymerase after removal of most of the 5' untranslated region, with the exception of 20 bp, as a 0.3 kb SmaI fragment. The K+ channel cDNA, Kv3.2b was employed as a negative control in the cAMP accumulation assay. The generation of Kv3.2b RNA was described by Luneau, et al, ((1991) *FEBS Letters* 1:163 167). Linearized plasmid templates were used with the STRATAGENE mCAP kit according to the manufacturer's protocol, except that the SP6 RNA polymerase reaction was performed at 40° C. Oocytes were harvested from mature female *Xenopus laevis*, treated with collagenase, and maintained at 18° C. in ND96 medium (GMCO) supplemented with 1 mM sodium pyruvate and 100 μg/mL gentamycin. Fifty nanoliters (10 ng) of RNA diluted in $H_2O$ was injected and oocytes were incubated at 18° C. for 48 hours.

EXAMPLE 6 cAMP Accumulation Assay in Oocytes

Oocytes injected with either human adenosine receptor transcript or the Kv3.2b transcript were transferred to fresh medium supplemented with 1 mM of the phosphodiesterase inhibitor, Ro 20-1724 (RBI, Natick, Mass.) and 1 mg/mL bovine serum albumin incubated for 30 minutes and transferred to an identical medium with or without the agonist adenosine (10 mM) for an additional 30 minutes at room temperature. Groups of 5–10 oocytes were lysed by transfer to ND96/100 mM HCl/1 mM Ro 20-1724 in microfuge tubes, shaken, incubated at 95° C. for 3 min, and centrifuged at 12000 g for 5 min. Supernatants were stored at −70° C. before CAMP measurements. Cyclic AMP levels were determined by radioimmunoassay (RIANEN kit, DuPont/NEN) using the acetylation protocol. The adenosine receptor antagonist, 8-(p-sulfophenyl) theophylline (100 FM) was utilized to inhibit the cAMP response induced by adenosine in oocytes expressing the adenosine receptors.

EXAMPLE 7 cAMP Accumulation in Stable CHO Cell Lines

The changes in cAMP accumulation can alternatively be measured in stably transfected CHO cells expressing the human adenosine receptor subtypes. CHO cells are washed twice in phosphate buffered saline (PBS) and detached in 0.2% EDTA in PBS. The cells are pelleted at 800 rpm for 10 min and resuspended in KRH buffer (140 mM NaCl/5 mM KCl/2 mM $CaCl_2$/1.2 mM $MgSO_4$/1.2 mM $KH_2PO_4$/6 mM glucose/25 mM Hepes buffer, pH 7.4). The cells are washed once in KRH buffer and resuspended at 107 cells/mL. The cell suspension (100 μl) is mixed with 100 μl of KRH buffer containing 200 uM Ro 20-1724 and incubated at 37° C. for 10 minutes. Adenosine (10 uM) was added in 200 μl KRH buffer containing 200 uM Ro 20-1724 and incubated at 37° C. for 20 minutes. After the incubation, 400 μl of 0.5 mM NaOAc (pH 6.2) was added and the sample was boiled for 20 minutes. The supernatant was recovered by centrifugation for 15 minutes and stored at −70° C. cAMP levels were determined by radiommunoassay (RIANEN kit, DuPont/NEN) using the to acetylation protocol. The effect of antagonists on cAMP accumulation are measured by preincubation for 20 minutes before adding adenosine.

EXAMPLE 8

Expression Construct and Transfection

The 1.7 kb HS-21a cDNA (A3) was subcloned as a SalI-BamHI fragment into the expression vector pCMV5 (Mumby, S. M., Heukeroth, R. O., Gordon, J. I. and Gilman, A. G. (1990) *Proc. Natl. Acad. Sci. USA* 87, 728–732.) creating the vector pCMV5-A3. CHO or HEK 293 cells stably expressing the human HS-21 a cDNA were prepared by co-transfection of 15 μg pCMV5-A3 and 1 μg pWLneo (Stratagene) using the calcium phosphate method. Stable cell lines were also generated using EBV based mammalian expression vectors, pREP (INVITROGEN). Neomycin resistant colonies were selected in 1 mg/mL G418 (GIBCO). Stable colonies were screened for expression of HS-21a by $^{125}I$-ABA binding.

EXAMPLE 9

Binding Studies

Membranes were prepared from stable CHO cell lines in 10 mM Hepes, pH 7.4 containing 0.1 mM benzamidine and 0.1 mM PMSF as described (Mahan, L. C. et al., (1991) *Mol. Pharinacol.* 40, 1–7). Pellets were resuspended in 5 mM Hepes, pH 7.4/5 mM $MgCl_2$/0.1 mM benzarnidine/0.1 mM PMSF at a protein concentration of 1–2 mg/mL and were incubated with adenosine deaminase (Boehringer Mannheim), 2 U/mL at 37° C. for 20 minutes. Saturation binding of $^{125}$I-ABA was carried out on 50 μg of membranes for 120 minutes at 25° C. in a total volume of 100 μl. The assay was terminated by rapid filtration and three washes with ice-cold binding buffer on a Skatron harvester equipped with a receptor binding filtermat (Skatron Instruments, Inc.). The specific activity of $^{125}$I-ABA, initially 2,200 Ci/mmol, was reduced to 100 Ci/mmol with nonradioactive I-ABA for saturation analysis. Nonspecific binding was measured in the presence of 1 uM I-ABA. The KD and Bmax values were calculated by the EBDA program (McPherson, G. A. (1983) Computer Programs for Biomedicine 17, 107–114). Competition binding of agonists and antagonists was determined with $^{125}$I-ABA (0.17–2.0 nM, 2000 Ci/mmol). Nonspecific binding was measured in the presence of 400 uM NECA. Binding data were analyzed and competition curves were constructed by use of the nonlinear regression curve fitting program Graph PAD InPlot, Version 3.0 (Graph Pad Software, San Diego). Ki values were calculated using the Cheng-Prusoff derivation (Cheng, Y. C. and Prusoff, H. R. (1973) *Biochem. Pharmacol.* 22, 3099–3108.).

Figure 2A:
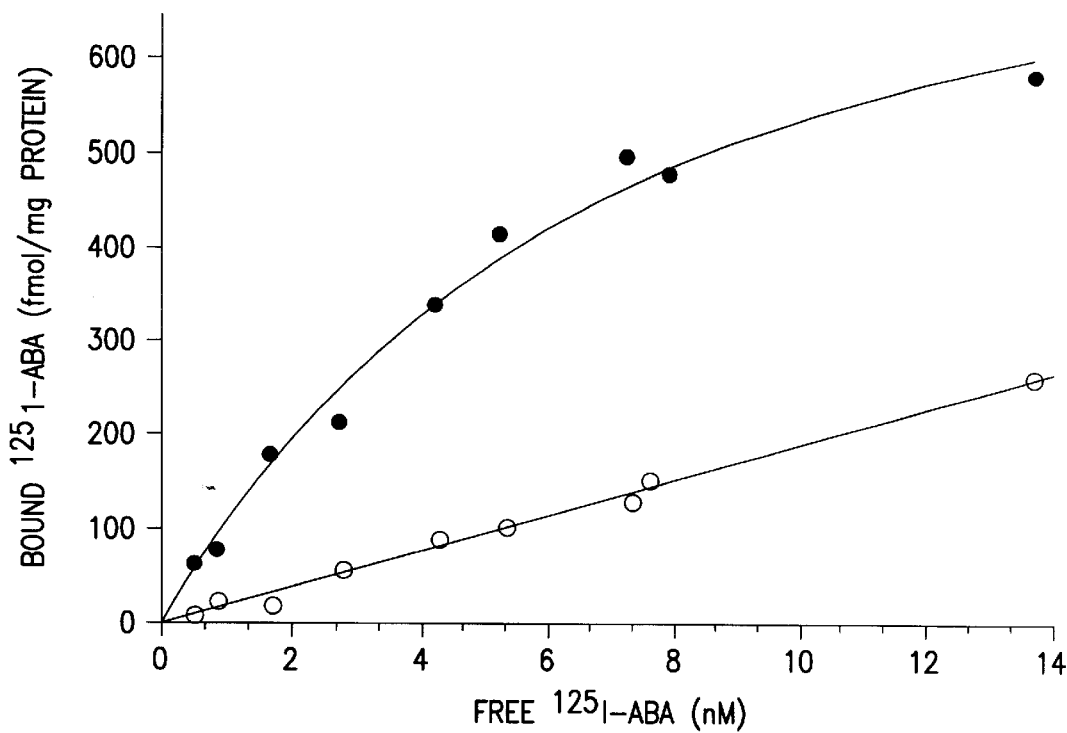
FIG. 2a shows the equilibrium binding of the radioligand $^{125}$I-ABA to membranes prepared from A3 stable transfected CHO cells shows specific (!) and non specific (") binding. Nonspecific binding was measured in the presence of 1 FM I-ABA.
Figure 2B:
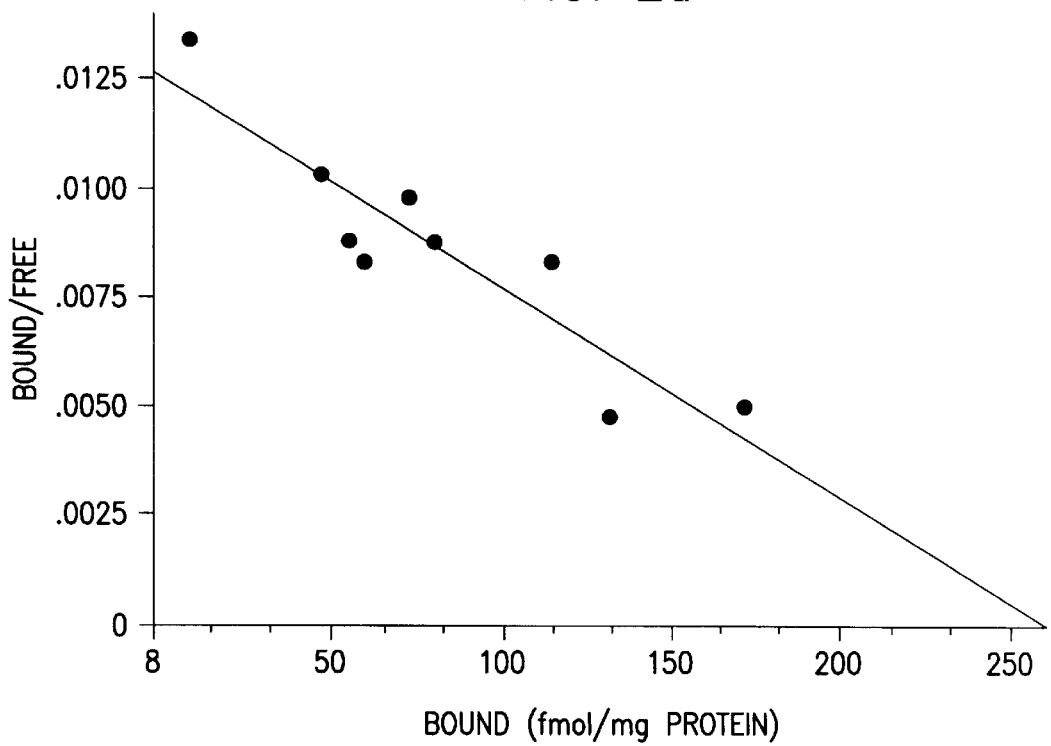
FIG. 2b shows the scatchard transformation of the specific binding.

The binding properties of the receptor encoded b HS-21a were evaluated on membranes prepared from CHO cells stably expressing the HS-21a cDNA. The radioligand, $^{125}$I-APNEA, was previously used to characterize rat A3 adenosine receptors. In preliminary experiments, high non-specific $^{125}$I-APNEA binding to CHO cell membranes was observed which interfered with the measurement of specific binding to expressed receptors. Specific and saturable binding of the adenosine receptor agonist, $^{125}$I-ABA was measured on membranes prepared from the stably transfected cells (FIG. 2a). The specific binding of $^{125}$I-ABA could be prevented by either 1 mM nonradioactive I-ABA or 400 uM NECA. No specific binding of $^{125}$I-ABA was measured on membranes prepared from non-transfected CHO cells. The specific binding of $^{125}$I-ABA measured in either the presence of 10 uM GTPγS or 100 mM Gpp(NH)p was reduced by 56 and 44% respectively, relative to the specific binding measured in the absence of the uncoupling reagents. These results suggest that $^{125}$I-ABA exhibits some agonist activity on the receptor encoded by the HS-21a cDNA expressed in the stable CHO cell line. $^{125}$I-ABA binds to membranes prepared from the HS-21a stable CHO cells with a dissociation constant of 10 nM (Bmax=258 fmol/mg protein) with a Hill coefficient of 0.99 indicating binding to a single class of high affinity sites (FIG. 2b).

Figure 3A:
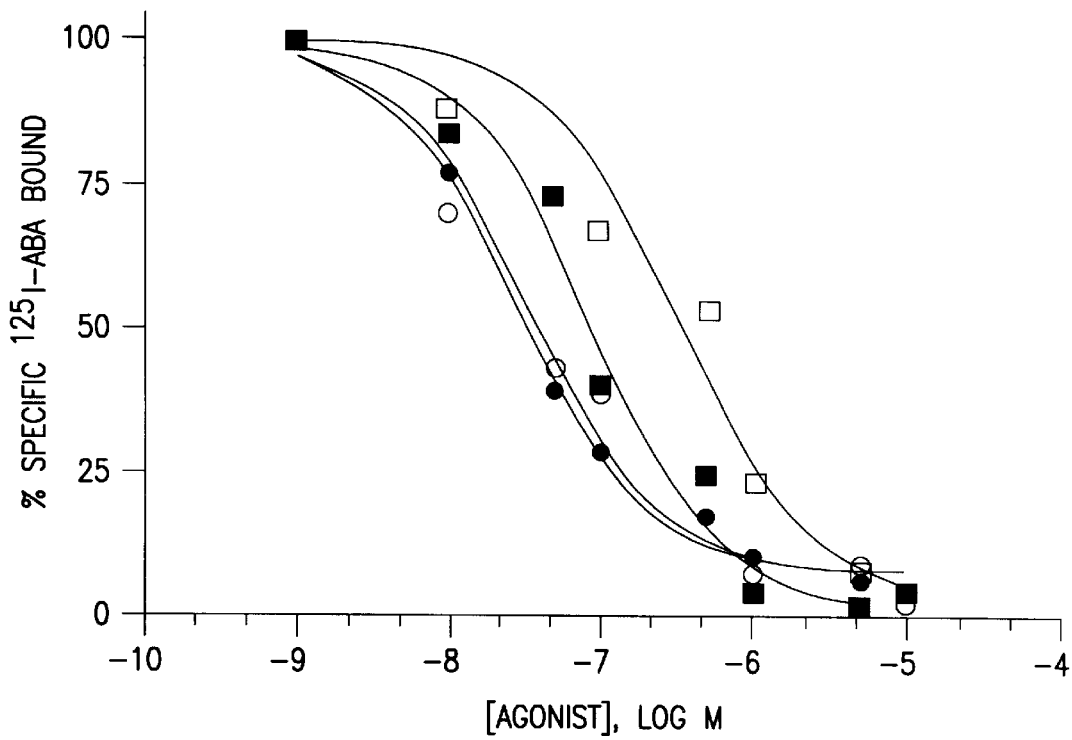
FIG. 3a and 3b show the competition by agonists and antagonists for $^{125}$I-ABA binding to membranes prepared from stably transfected CHO cells expressing the human A3 adenosine receptor. Agonists (FIG. 3a), (!) NECA, (") R-PIA, (#) CPA, (R) S-PIA; antagonists (FIG. 3b), (!) I-ABOPX, (#) BW-A 1433, (") XAC, (R) DPCPX.
Figure 3B:
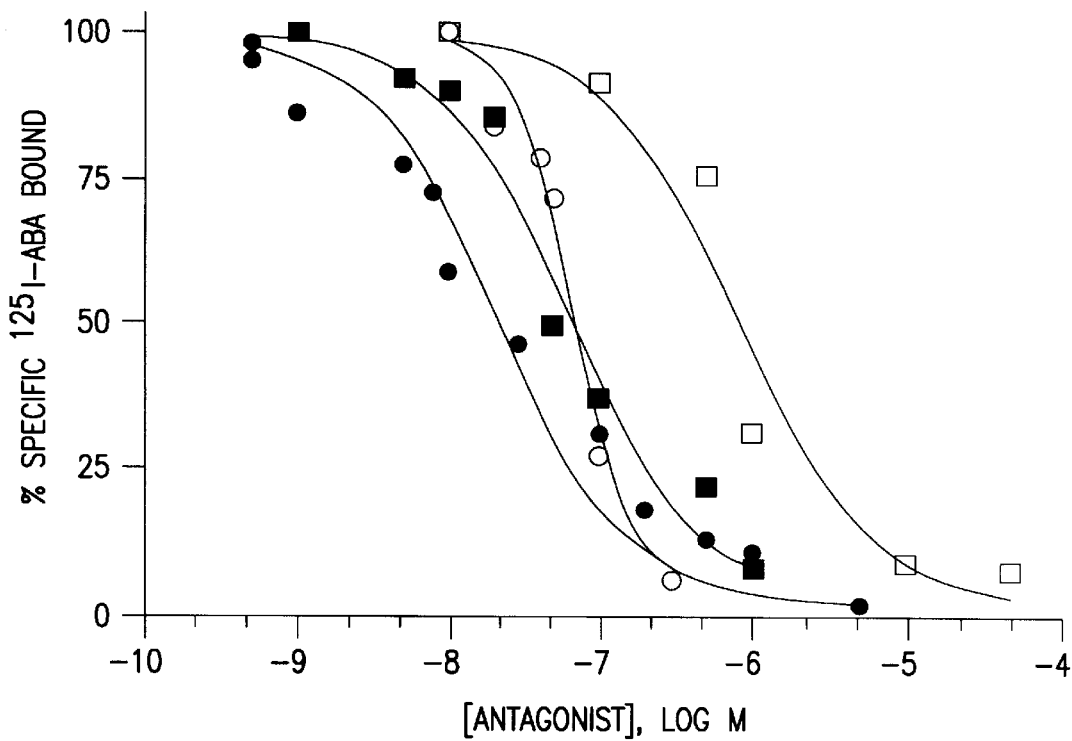

The competition of adenosine receptor agonists and antagonists for binding to HS-21a receptors was determined. The Ki values for agonists (FIG. 3a) were calculated to be 26 nM for NECA, 34 nM for R-PIA, 89 nM for CPA and 320 nM for S-PIA, resulting in a potency order profile of NECA>R-PIA>CPA>S-PLA. In contrast to the insensitivity of adenosine receptor antagonists reported for the rat A3 adenosine receptor subtype, a number of xanthine antagonists exhibited competition with $^{125}$I-ABA for binding to the HS-21 a receptor (FIG. 3b). Studies of the sheep A3 adenosine receptor indicated that 8-phenylxanthines substituted in the para-position with acidic substituents are high affinity antagonists. By evaluating additional xanthines in this class we determined that I-ABOPX is the highest affinity para-substituted antagonist yet reported for A3 adenosine receptors. On the other hand, the meta-substituted antagonist BS-3911 proved to be a potent and selective A3 antagonist with Ki values as follows for recombinant human adenosine receptors;

A1: 830"280
A2A: 323"100
A2B 1221"378
A3 17.5"7.6

Hence, compared to the human A1, A2A, and A2B receptors, BW-3911 is 47, 18 and 70-fold more selective, respectively, for A3 receptors. Adenosine, adenosine metabolites and other A3 adenosine receptor agonists induce mast cell degranulation in an animal model; this can be prevented by selective antagonisms of the A3 receptor. The release of enzymes, bioactive amines and arachidonic acid metabolites following mast cell activation causes vasoconstriction, edema, leukocyte accumulation, and ultimately, tissue damage. Mast cell degranulation is a component of: myocardial reperfusion injury, hypersensitivity reactions (asthma, allergic rhinitis, and urticaria), ischemic bowel disease, autoimmune inflammations, 20 and atopic dermatitis. The present invention relates to the use of highly specific meta-substituted 8-phenylxanthine A3 adenosine receptor antagonists to treat or prevent these diseases and pathologic effects that result from mast cell degranulation.

While the foregoing specification teaches the principles of the present invention, with examples provided for the purpose of illustration, it will be understood that the practice of the invention encompasses all of the variations, adaptations, modifications as come within the scope of the following claims and their equivalents.

ABBREVIATIONS

[3H]-CHA, [3H]-cyclohexyladenosine;
[3H]-NECA, [3H]-5'-N-ethylcarboxamido-adenosine;
$^{125}$I-ABA, $N^6$-(4-amino-3$^{125}$iodobenzyl)adenosine;
$^{125}$I-APNEA, $N^6$-2-(4-amino-3$^{125}$iodophenyl) ethyladenosine;
NECA, N-ethylcarboxamidoadenosine;
CGS21680, 2-[4-(2-carboxyethyl) phenyllethylamino-5'-N-ethylcarboxamidoadenosine;
(R,S)-PIA, (R,S)-$N^6$-phenyl-2-propyladenosine;
CPA, $N^6$-cyclopentyladenosine;
I-ABOPX, (3-(3-iodo-4-aminobenzyl)-8-(4-oxyacetate) phenyl-1-propylxanthine;
BW-A 1433, 1,3 -dipropyl-8-(4-acrylate) phenylxanthine;
XAC, xanthine amine cogener;
DPCPX, 1,3-dipropyl-8-cyclopentylxanthine;
GTPS, guanosine 5'-O-3-thiotriphosphate;
Gpp(NH)p, 5'- guanylimidodiphosphate;
G protein, guanine nucleotide-binding proteins.

REFERENCES

1. Van Caulker, D., Muller, M. and Hamprecht, B. (1979) *J. Neurochem.* 33, 999–1005.
2. Bruns, R. F., Lu, G. H. and Pugsley, T. A. (1986) *Mol. Pharmacol.* 29, 331–346.
3. Wan, W., Sutherland, G. R. and Geiger, J. D. (1990) *J. Neurochem.* 55, 1763–1771.
4. Linden, J., Jacobson, M. A., Hutchins, C. and Williams, M. (1994) Adenosine Receptors in Handbook of Receptors and Channels, Vol 1. G Protein-Linked Receptors, ed Peroutka, D. J. (CRC Press, Boca Raton. Fla.), p.29–43.

5. Meyerhof, W., Muller-Brechlin, R. and Richter, D. (1991) *FEBS Lett.* 284, 155–160.
6. Zhou, Q-Y, Chuanyi, L., Olah, M. E., Johnson, R. A., Stiles, G. L. and Civelli, (1992) *Proc. Natl. Acad. Sci. USA* 89 7432–7436.
7. Linden, J. Taylor, H. E., Robeva, A. S., Tucker, A. L., Stehle, J. H., Rivkees, S. A., Fink, S. J. and Reppert, S. M., (1993) *Mol. Pharm.* 44:524–532.
8. Libert, F., Van Sande, J., Lefort, A., Czemilofsky, A., Dumont, J. E., Vassart, G., Ensinger, H. A. and Mendla, K. D. (1992) *Biochem. Biophys. Res. Comm.* 187, 919–926.
9. Furlong, T. J., Pierce, K. D., Selbie, L. A. and Shine, J. (1992) *Mol Brain. Res.* 15, 62–66.
10. Pierce, K. D., Furlong, T. J., Selbie, L. A. and Shine, J. (1992) *Biochem. Biophys. Res. Comm.* 187, 86–93.
11. Salvatore, C. A., Luneau, C. J., Johnson, R. G. and Jacobson, M. A. (1992) *Int. J. Pur. Pyrid Res.* 3, 82.
12. Linden, J., Patel, A. and Sadek, S. (1985) *Cir. Res.* 56, 279–284.
13. Linden, J., Patel, A., Earl, C. Q., Craig, R. H. and Daluge, S. M. (1988) *J. Med. Chem.* 31, 745–751.
14. Sanger, F. S., Nicklen, S. and Coulson, A. R. (1977) *Proc. Natl. Acad. Sci. USA* 74, 5463–5467.
15. Feinberg, A. and Vogelstein., B. (1983) *Anal. Biochem.* 132, 6–13.
16. Mumby, S. M., Heukeroth, R. O., Gordon, J. I. and Gilman, A. G. (1990) *Proc. Natl. Acad. Sci. USA* 87, 728–732.
17. Mahan, L. C., McVittie, L. D., Smyk-Randall, E. M., Nakata, H., Monsma, F. J., Gerfen, C. R. and Silbey, D. R. (1991) *Mol. Pharmacol.* 40, 1–7.
18. McPherson, G. A. (1983) *Computer Programs for Biomedicine* 17, 107–114.
19. Cheng, Y. C. and Prusoff, H. R. (1973) *Biochem. Phannacol.* 22, 3099–3108.
20. Hamilton, B. R. and Smith, D. O. (1991) *J. Physiol. (Lond.)* 432, 327–341.
21. Schild, H. O. (1957) *Pharm. Rev.* 9, 242–246.
22. Sambrook, J., Fritsch, E. and Maniatis, T. (1989) *Molecular Cloning: A Laboratory Manual,* Second Edition, (Cold Spring Harbor Press, Cold Spring Harbor, N.Y.).
23. Strosberg, A. D. (1991) *Eur. J. Biochem.* 196, 1–10.
24. O'Dowd, B. F., Hnatowich, M., Caron, M. G., Lefkowitz, R. J. and Bouvier, M. (1989) *J. Biol. Chem.* 264, 7564–7569.
25. Dodd, P. R., Watson, W. E. J., and Johnston, G. A. R. (1986) *Clin. Exp. Pharmacol. Physiol.* 13, 711–722.
26. Schiffmann, S. N., Libert, F., Vassart, G. and Vanderhaeghen, J. J. (1991) *Neurosci. Lett.* 130, 177–181.
27. Peet, N. P., Lentz, N. L., Meng, E. C., Dudley, M. W., Ogden, A. M. L., Demeter, D. A., Weintraub, H. J. R. and Bey, P. (1990)) *J. Med Chem.* 33, 3127–3130.
28. Van der Wenden, E. M., IJzerinan, A. P. and Soudijn, W. (1992) *J. Med Chem.* 35, 629–635.
29. Stehle, J. H., Rivkees, S. A., Lee, J J., Weaver, D. R., Deeds, J. D. and Reppert, S. M. (1992) *Mol. Endocrinol.* 6, 384–393.
30. Fozzard, J. R. and Carruthers, A. M. (1993) *Br. J. Pharmacol.* 109, 3–5.
31. Neely, C. F., Kadowitz, P. J., Lippton, H., Neiman, M. and Hyman, A. (1989) *J. Pharmacol. Exp. Ther* 250, 170–176.
32. Konduri, G. G., Woodward, L. L., Mukhopadhyay, A. and Deslunukh, D. R. (1992) *Am. Rev. Respir. Dis.* 146, 670–676.
33. Cushley, M. J., Tattersfield, A. E. and Holgate, S. T. (1984) *Am. Rev. Respir. Dis.* 129, 380–384.

What is claimed is:

1. A method for blocking the vasoconstrictive response induced through adenosine activation of the $A_3$ adenosine receptor subtype, comprising administering to a mammal in need of said method, an effective amount of a compound of the formula:

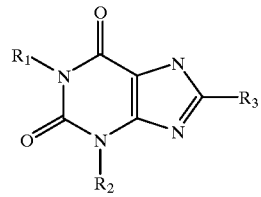

wherein $R_1$ is propyl; $R_2$ is propyl; and $R_3$ is phenyl-3-acrylate; or a pharmaceutically acceptable salt thereof.

2. A method for treating or preventing myocardial ischemia, inflammation, brain arteriole diameter constriction, or the release of allergic mediators in a mammal in need of said method comprising administering to said mammal, an effective amount of a compound of the formula:

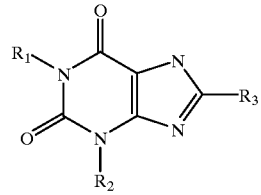

wherein $R_1$ propyl; $R_2$ is propyl; and $R_3$ is phenyl-3-acrylate; or a pharmaceutically acceptable salt thereof.

3. A method for preventing or treating asthma, bronchoconstriction, allergic potentiation, inflammation or reperfusion injury in a human in need of said method comprising administering to said human, an effective amount of a compound of the formula:

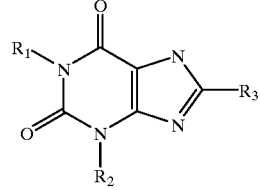

wherein $R_1$ is propyl; $R_2$ is propyl; and $R_3$ is phenyl-3-acrylate; or a pharmaceutically acceptable salt thereof.

4. A method for preventing mast cell degranulation in a human in need of said method comprising administering to said human, an effective amount of a compound of the formula:

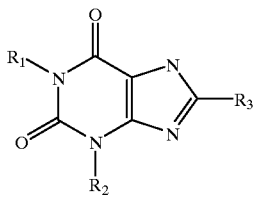

wherein R₁ is propyl; R₂ is propyl; and R₃ is phenyl-3-acrylate; or a pharmaceutically acceptable salt thereof.

5. A method for achieving blockade of vascular constriction induced by activation of an $A_3$ subtype receptor in a primate comprising administering to said primate, an effective amount of a compound of the formula:

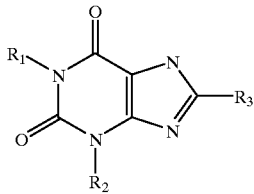

wherein R₁ is propyl; R₂ is propyl; and R₃ is phenyl-3-acrylate; or a pharmaceutically acceptable salt thereof.

6. A method for treating Addison's disease, autoimmune hemolytic anemia, Crohn's disease, Goodpasture's syndrome, Grave's disease, Hashimoto's thyroiditis, idiopathic thrombocytopinic purpura, insulin-dependent diabetes millitus, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, or systemic lupus erythematosus in a human, comprising administering to said human, an effective amount of a compound of the formula:

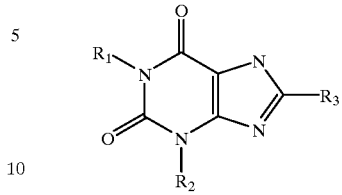

wherein R₁ is propyl; R₂ is propyl; and R₃ is phenyl-3-acrylate; or a pharmaceutically acceptable salt thereof.

7. A therapeutic method for treating or preventing a disease mediated through activation of the $A_3$ subtype of the adenosine receptor on mast cells in a human in need of said method, comprising administering to said human, an effective amount of a compound of the formula:

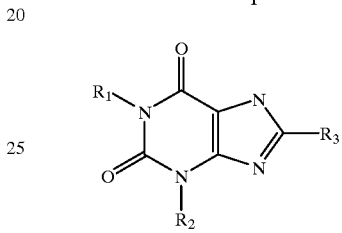

wherein R₁ is propyl; R₂ is propyl; and R₃ is phenyl-3-acrylate; or a pharmaceutically acceptable salt thereof.

8. The method of claim 7 wherein the disease is asthma, myocardial reperfusion injury, rhinitis, poison ivy induced responses, urticaria, scleroderma, arthritis, or an inflammatory bowel disease.

* * * * *

UNITED STATES PATENT AND TRADEMARK OFFICE
CERTIFICATE OF CORRECTION

PATENT NO.    : 6,303,619 B1
DATED         : October 16, 2001
INVENTOR(S)   : Linden It is certified that error appears in the above-identified patent and that said Letters Patent is hereby corrected as shown below:

Column 4,
Line 60, delete "Such" and insert -- such --, therefor.

Column 15,
Line 11, delete "11" and insert -- h --, therefor.
Line 32, delete "-aminiobenizyladenosine (125I-ABA)" and insert
-- -aminobenzyladenosine ($^{125}$I-ABA) --, therefor.

Column 20,
Line 41, after "$R_1$" insert -- is --.

Signed and Sealed this

Twenty-seventh Day of August, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,303,619 B1 | Page 1 of 1 |
| APPLICATION NO. | : 09/038991 | |
| DATED | : October 16, 2001 | |
| INVENTOR(S) | : Linden | |

It is certified that error appears in the above-identified patent and that said Letters Patent is hereby corrected as shown below:

On the face page, in field (73), in column 1, lines 1 – 3, delete "Assignees: University of Virginia; University of Virginia Patent Foundation, both of Charlottesville" and insert -- Assignee: University of Virginia Patent Foundation, Charlottesville, VA. --, therefor.

Signed and Sealed this

Seventeenth Day of April, 2007

JON W. DUDAS
*Director of the United States Patent and Trademark Office*